(12) United States Patent
Chapin et al.

(10) Patent No.: US 7,177,391 B2
(45) Date of Patent: Feb. 13, 2007

(54) IMAGING INSPECTION APPARATUS

(75) Inventors: Fletcher L. Chapin, Maine, NY (US); John E. Kozol, Binghamton, NY (US)

(73) Assignee: SureScan Corporation, Endicott, NY (US)

( * ) Notice: Subject to any disclaimer, the term of this patent is extended or adjusted under 35 U.S.C. 154(b) by 0 days.

(21) Appl. No.: 11/091,521

(22) Filed: Mar. 29, 2005

(65) Prior Publication Data

US 2006/0227932 A1  Oct. 12, 2006

(51) Int. Cl.
*G01N 23/04* (2006.01)
(52) U.S. Cl. ...................................... 378/57; 250/360.1
(58) Field of Classification Search ................. 378/57; 250/358.1, 359.1, 360.1
See application file for complete search history.

(56) References Cited

U.S. PATENT DOCUMENTS

| 3,616,893 | A |   | 11/1971 | Knadle et al. |        |
|-----------|---|---|---------|---------------|--------|
| 4,020,346 | A | * | 4/1977  | Dennis        | 378/57 |
| 4,157,623 | A |   | 6/1979  | Satterwhite   |        |
| 4,160,501 | A | * | 7/1979  | Johannsen     | 198/632|
| 4,183,158 | A |   | 1/1980  | Satterwhite   |        |
| 4,266,650 | A |   | 5/1981  | Patel et al.  |        |
| 5,020,086 | A |   | 5/1991  | Peugeot       |        |
| 5,026,983 | A |   | 6/1991  | Meyn          |        |
| 5,259,012 | A |   | 11/1993 | Baker et al.  |        |
| 5,297,665 | A |   | 3/1994  | Smith et al.  |        |
| 5,367,552 | A |   | 11/1994 | Peschmann     |        |
| 5,483,569 | A |   | 1/1996  | Annis         |        |
| 5,524,133 | A |   | 6/1996  | Neale et al.  |        |
| 5,583,904 | A |   | 12/1996 | Adams         |        |
| 5,629,966 | A |   | 5/1997  | Dykster et al.|        |
| 5,991,358 | A |   | 11/1999 | Dolazza et al.|        |
| 6,018,562 | A |   | 1/2000  | Willson       |        |
| 6,052,433 | A |   | 4/2000  | Chao          |        |
| 6,129,196 | A |   | 10/2000 | Lapper et al. |        |
| 6,236,709 | B1| * | 5/2001  | Perry et al.  | 378/57 |
| 6,708,814 | B2|   | 3/2004  | Wagstaffe     |        |
| 2003/0121761 | A1 |  | 7/2003 | Wagstaffe     |        |

FOREIGN PATENT DOCUMENTS

EP  0 918 026 A1  5/1999
WO  01/22071 A2  3/2001

OTHER PUBLICATIONS

Pretzler et al., Translation of EP 0918026 A1.*

* cited by examiner

*Primary Examiner*—Edward J. Glick
*Assistant Examiner*—Chih-Cheng Glen Kao
(74) *Attorney, Agent, or Firm*—Hinman, Howard & Kattell, LLP; Lawrence R. Fraley

(57) ABSTRACT

An imaging inspection apparatus which utilizes a plurality of individual imaging inspection devices (e.g., X-ray Computer Tomography scanning devices) positioned on a frame for directing beams onto articles having objects therein to detect the objects based on established criteria. The apparatus utilizes a conveyor which is not physically coupled to the frame having the imaging inspection devices to pass the articles along a path of travel to an inspection location within the apparatus, whereupon the inspection devices direct beams onto the article and the beams are detected and output signals provided to a processing and analysis assembly which analyzes the signals and identifies certain objects which meet the criteria.

11 Claims, 4 Drawing Sheets

IMAGING INSPECTION APPARATUS

TECHNICAL FIELD

The invention relates to inspection apparatus designed for inspecting articles such as luggage, baggage, mail, etc. More particularly, the invention relates to such apparatus which utilize X-ray imaging and the like.

BACKGROUND OF THE INVENTION

The use of imaging inspection apparatus is known, including those which utilize X-ray imaging. Such apparatus are used to inspect articles such as personal luggage of airplane travelers at airports for such undesirable items as explosives and drugs.

One particularly successful example of such apparatus is that which utilizes what is referred to in the art as "X-ray Computer Tomography" (hereinafter also referred to as, simply, XCT). XCT apparatus are in wide use in the medical field for providing medical imaging such as patient body X-rays. XCT (often referred to in the medical profession simply as "CT scanning") produces a cross sectional image from a grouping of attenuation measurements taken at different angles about an object such as a patient's chest or head, while the patient is maintained in a stationary position.

Modifications have been made to such apparatus to make these adaptable to taking images for non-medical purposes. In U.S. Pat. No. 5,367,552, issued Nov. 22, 1994, for example, a rotating XCT scanning unit is used which requires an object to remain stationary during scanning. This apparatus is designed for detecting concealed objects, such as explosives, drugs, or other contraband in a person's luggage. The apparatus uses scanning to identify concealed objects with a density corresponding to the density of target objects such as explosives or drugs. To reduce the amount of scanning required, a number of pre-scanning approaches are described in this patent. Based upon pre-scan data, selected locations for scanning are identified. The resulting scan data is utilized to automatically identify objects of interest, which identification is further verified through automatic analysis of such attributes as shape, texture, context, and X-ray diffraction. The objects of interest are then reconstructed and displayed on a computer monitor for visual analysis by the apparatus operator.

In order to make such apparatus capable of even higher speed scanning, such as that useful for scanning the luggage of large numbers of travelers in a relatively shorter time period than provided by conventional stationary apparatus, even further modifications have been made. One such apparatus is described in U.S. Pat. No. 6,236,709, issued May 22, 2001, in which a continuous, XCT imaging system includes a conveyor which moves a closed package for being scanned along the conveyor past three spaced sensing stations. At each sensing station a plurality of X-ray sources each emit a fan beam in the same scan plane which passes through the package to a plurality of detectors opposite the X-ray sources. One scan is a vertical perpendicular scan plane relative to the direction of travel of the package along the conveyor belt and the remaining two scan planes are horizontal scan planes at right angles and transverse to the direction of travel. One horizontal scan plane is a left to right scan plane while the remaining scan plane is a right to left scan plane. Each detector provides multiple energy outputs for the same data point in a scan slice, and the detector outputs are stored until all three sensing stations have scanned the same cross sectional view of the package in three directions. Scans are sequentially taken as the package moves continuously through the sensing stations and scanned data corresponding to cross sectional views of the package is accumulated. The stored data is calibrated and normalized and then used in a Computer Tomographic algebraic reconstruction technique. This is described in this patent as a "multi-spectral CT reconstruction", where the density of a reconstructed object is determined by the attenuation which it causes in the scanning X-rays while the atomic number of the object is determined from the multiple energy scan output. In a classifier, the density and atomic number are compared to a table containing density and atomic number identification values for specific objects to be located.

Other examples of various scanning apparatus systems, including those with and without conveyors, are shown and described in the following U.S. Patents.

In U.S. Pat. No. 6,052,433, issued Apr. 18, 2000, there is described an apparatus for performing dual-energy X-ray imaging using two-dimensional detectors. The apparatus consists of an X-ray source, a 2-dimensional X-ray detector, a beam selector, and a second 2-dimensional X-ray detector. The subject is located between the X-ray source and first detector. The beam selector prevents primary X-rays from reaching selected locations of the second (rear) detector. A pair of primary dual-energy images is obtained at the rear detector. Using a dual-energy data decomposition method, a low-resolution primary X-ray first detector image is calculated, from which a high-resolution primary dual-energy image pair is calculated. In addition, the data decomposition method is used to calculate a pair of high-spatial-resolution material composition images.

In U.S. Pat. No. 6,018,562, issued Jan. 25, 2000, there is described an apparatus for automatic recognition and identification of concealed objects and features thereof, such as contraband in baggage or defects in articles of manufacture. The apparatus uses multiple energy X-ray scanning to identify targets with a spectral response corresponding to a known response of targets of interest. Detection sensitivity for both automatic detection and manual inspection are improved through the multiple-energy, multi-spectral technique. Multi-channel processing is used to achieve high throughput capability. Target identification may be verified through further analysis of such attributes as shape, texture, and context of the scan data. The apparatus uses a statistical analysis to predict the confidence level of a particular target identification. A radiograph, CT image, or both may be reconstructed and displayed on a computer monitor for visual analysis by the apparatus operator. Finally, the apparatus may receive and store input from the operator for use in subsequent target identification.

In U.S. Pat. No. 5,991,358, issued Nov. 23, 1999, there is described a data acquisition system for use in a CT scanner which consists of an analog-to-digital converter for generating digital signals in response to analog signals representative of projection data taken at a relatively constant sampling rate. The apparatus also uses an interpolation filter for generating projection data for a plurality of predetermined projection angles as a function of the digital signals irrespective of the sampling rate. This patent references a known system which includes an array of individual detectors disposed as a single row in the shape of an arc of a circle having a center of curvature at a certain point, referred to as the "focal spot", where the radiation emanates from the X-ray source. The X-ray source and the array of detectors in this known system are positioned so that the X-ray paths between the source and each of the detectors all lie in the same plane (hereinafter the "rotation plane" or "scanning plane") which is normal to the rotation axis of the disk. Since the X-ray paths originate from what is substantially a point source and extend at different angles to the detectors, the X-ray paths form a "fan beam." The X-rays incident on a single detector at a measuring interval during a scan are commonly referred to as a "ray", and each detector generates an analog output signal indicative of the intensity of its corresponding ray. Since each ray is partially attenuated by all the mass in its path, the analog output signal generated by each detector is representative of an integral of the density of all the mass disposed between that detector and the X-ray source (i.e., the density of the mass lying in the detector's corresponding ray path) for that measuring interval.

In U.S. Pat. No. 5,629,966, issued May 13, 1997, there is described a real time radiographic test system which consists of a protective housing and a conveyor for conveying articles to be tested through the housing. A real time radiographic test instrument is located in the housing for performing a real time radiographic test on the article. The test instrument includes X-ray equipment disposed for directing an X-ray beam within the housing in a direction which does not intersect the conveyor. An article-handling actuator is located in the housing for repositioning an article from the conveyor to a position in registry with the X-ray beam, for maintaining the article in registry with the X-ray beam while the real time radiographic test is performed on the article and thereafter returning the article to the conveyor. The article-handling actuator and the X-ray equipment are designed such that each article to be tested is positioned substantially identically relative to the X-ray beam.

In U.S. Pat. No. 5,583,904, issued Dec. 10, 1996, there is described a laminography system that allows generation of high speed and high resolution X-Ray laminographs by using a continuous scan method with two or more linear detectors and one or more collimated X-ray sources. Discrete X-ray images, with different viewing angles, are generated by each detector. The discrete X-ray images are then combined by a computer to generate laminographic images of different planes in the object under test, or analyzed in such a manner to derive useful data about the object under test. This system does not require any motion of the source or detectors, but simply a coordinated linear motion of the object under test. Higher speed is achieved over conventional laminography systems due to the continuous nature of the scan, and due to the ability to generate any plane of data in the object under test without having to re-image the object.

In U.S. Pat. No. 5,524,133, issued Jun. 24, 1996, there is described an X-ray analysis device for determining the mean atomic number of a material mass by locating a broad band X-ray source on one side of a testing station and on the other, a detector, comprising a target having X-ray detectors positioned adjacent thereto. One of the detectors is positioned and adapted to receive X-rays scattered by the detector target in a generally rearward direction and the other detector is positioned and adapted to detect forwardly propagating X-rays scattered off axis typically by more than 30 degrees, due to so-called "Compton scatter." Each of the X-ray detectors provides signals proportional to the number of X-ray photons incident thereon. The apparatus further includes means responsive to the two detector outputs which form a ratio of the number of photons detected by the two detectors and forms a numerical value thereof. A look-up table containing mean atomic numbers for given numerical ratios for different materials is used, as is a means for determining from the look-up table the atomic number corresponding to the numerical ratio obtained from the outputs of the two detectors. The atomic number is provided as an output signal.

In U.S. Pat. No. 5,483,569, issued Jan. 9, 1996, there is described an inspection system for inspecting objects with "penetrating radiation" having a conveyor with first and second portions which are separated by a gap. Illumination by this radiation is provided in a scanning plane which is located in the gap, and the system may be used for the inspection of thin objects. Additionally, the illumination may be arranged in the inspection of normal size objects, e.g., suitcases or cargo boxes, so that it does not include a ray which is perpendicular to any face of the object. Further, the relative orientation of the scanning plane and the faces of the object may be arranged so that the illumination does not include a ray which is parallel to any face of the object. A scanning configuration wherein the illumination does not include a ray which is perpendicular or parallel to any face of an object having parallel faces, for example, a rectangular solid, results in a display projection of the object which appears to be three dimensional.

In U.S. Pat. No. 5,259,012, issued Nov. 2, 1993, there is described a system which enables multiple locations within an object to be imaged without mechanical movement of the object. The object is interposed between a rotating X-ray source and a synchronized rotating detector. A focal plane within the object is imaged onto the detector so that a cross-sectional image of the object is produced. The X-ray source is produced by deflecting an electron beam onto a target anode. The target anode emits X-ray radiation where the electrons are incident upon the target. The electron beam is produced by an electron gun which includes X and Y deflection coils for deflecting the electron beam in the X and Y directions. Deflection voltage signals are applied to the X and Y deflection coils, and cause the X-ray source to rotate in a circular trace path. An additional DC voltage applied to the X or Y deflection coil will cause the circular path traced by the X-ray source to shift in the X or Y direction by a distance proportional to the magnitude of the DC voltage. This causes a different field of view, which is displaced in the X or Y direction from the previously imaged region, to be imaged. Changes in the radius of the X-ray source path result in a change in the Z level of the imaged focal plane.

In U.S. Pat. No. 5,026,983, issued Jun. 25, 1991, there is described an apparatus for examining food products for undesired ingredients by means of laser irradiation. A laser beam scans the food products according to a predetermined pattern. Variations in the intensity of the laser beam passing through the food products indicate the presence of undesired ingredients. This method is carried out by an apparatus which comprises two parabolic mirrors, a laser emitting a laser beam so as to originate from the focus of one of the mirrors and a detection means positioned in the focus of the other mirror. The food products are moved between the mirrors by conveyor belts.

In U.S. Pat. No. 5,020,086, issued May 28, 1991, an object is scanned by an X-ray beam from a circular position on a target resulting from the electron beam being scanned in a circle by appropriate control signals from a beam controller and applied to the deflection coils of a microfocus X-ray tube. Tomosynthesis is accomplished by the well-known method of in-register combination of a series of digital X-ray images produced by X-ray beams emanating from different locations. This is achieved by positioning an X-ray source at multiple points on a circle around a central axis. This system eliminates some mechanical motion in that the detector does not have to rotate. However, practical limitations of pixel size and resolution tend to limit this system to inspection of items with small fields of view. Additionally, the system still requires an X, Y table to position the object under the field of view.

The above patents are incorporated herein by reference.

The accurate, rapid inspection of moving articles such as multiple luggage pieces, often having many different sizes and shapes, is, understandably, a relatively difficult task, as indicated by just some of the difficulties mentioned in some of the above patents and elsewhere in the literature pertaining to this art with respect to articles in both stationary and moving positions. Undesirable movement of such articles along the path on which these travel may result in erroneous readings. In large apparatus in which a conveyor is the best means of such article transport, undesirable vibrations or other motion by the parts of the conveyor (e.g., the rollers, belts, drive motor) may contribute to such errors.

The present invention defines a new and unique inspection apparatus which, in one embodiment, uses imaging technology (e.g., XCT scanning) in combination with a moving conveyor which substantially prevents undesirable motion to the articles moving along the conveyor and being inspected. The apparatus is thus able to effectively inspect (e.g., scan) articles because the articles move along its conveyor in a smooth manner during inspection.

It is believed that such an inspection apparatus would constitute a significant advancement in the art.

OBJECT AND SUMMARY OF THE INVENTION

It is a primary object of the present invention to enhance the imaging inspection apparatus art.

It is another object of the invention to provide an imaging inspection apparatus which enables facile inspection of articles moving along a conveyor with articles substantially not being subjected to undesirable vibrations and/or other forces.

It is yet another object of the invention to provide such an imaging inspection apparatus which can be reduced in length from its normal operating orientation, e.g., to enhance shipping of the apparatus.

According to one aspect of the invention, there is provided an imaging inspection apparatus for inspecting objects located within moving articles, the imaging inspection apparatus comprising a conveyor for conveying articles having objects located therein along a line of travel through an inspection location located substantially within said imaging inspection apparatus, the conveyor being of a substantially flat orientation during said conveying of said articles, a frame structure, a plurality of imaging inspection devices positioned on said frame and adapted for directing beams onto the articles as the articles move on said conveyor and pass along the path of travel through said inspection location to thereby inspect the articles, and for providing output signals as a result of this inspecting, and a processing and analysis assembly adapted for receiving the output signals from the plurality of imaging inspection devices and for analyzing the output signals to identify the objects within the moving articles. The conveyor is not physically coupled to the frame structure and is also adapted for being folded to a non-flat orientation of a lesser length than its flat orientation when the conveyor is not conveying the articles along the path of travel.

BEST MODE FOR CARRYING OUT THE INVENTION

For a better understanding of the present invention, together with other and further objects, advantages and capabilities thereof, reference is made to the following disclosure and appended claims in connection with the above-described drawings. Like figure numbers will be used from FIG. to FIG. to identify like elements in these drawings.

Figure 1:
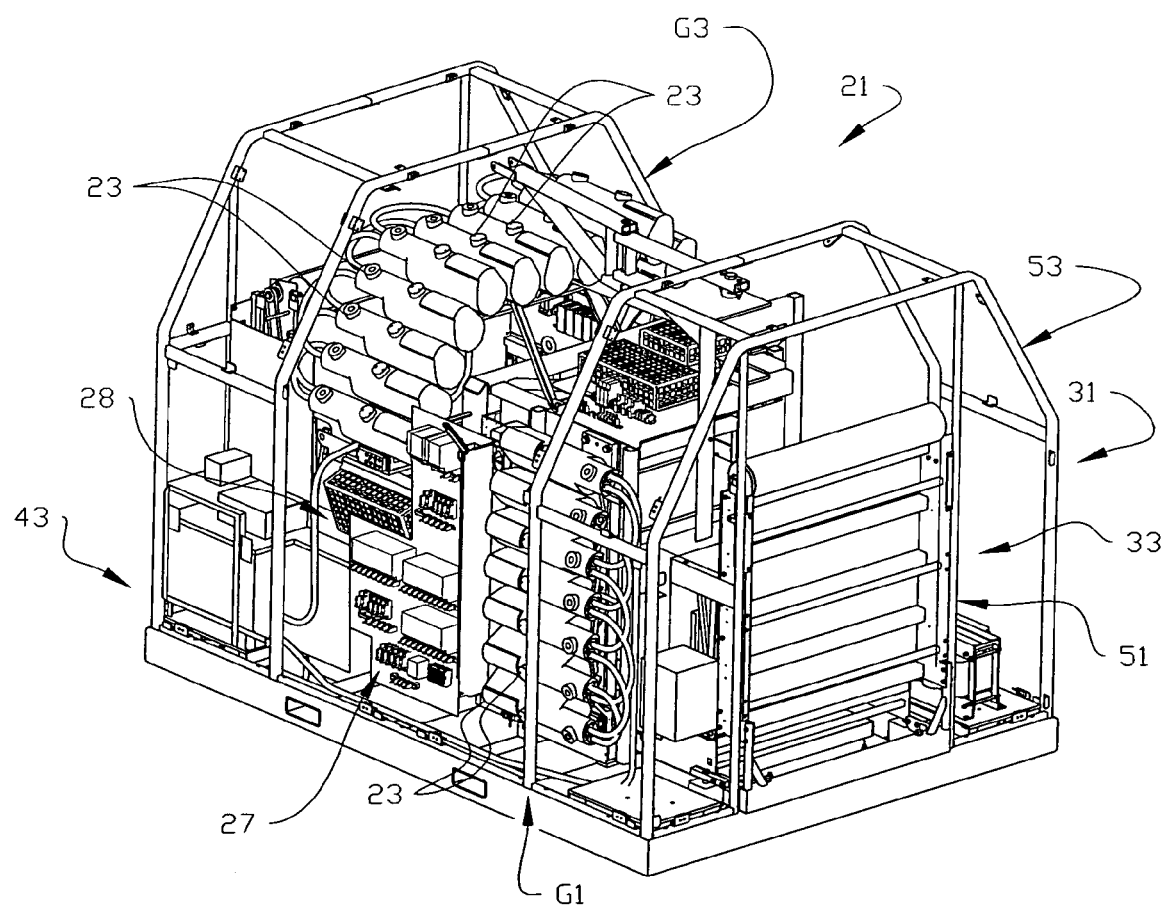
FIG. 1 is a front perspective view of an imaging inspection apparatus for inspecting objects located within moving articles, according to one embodiment of the invention.
Figure 2:
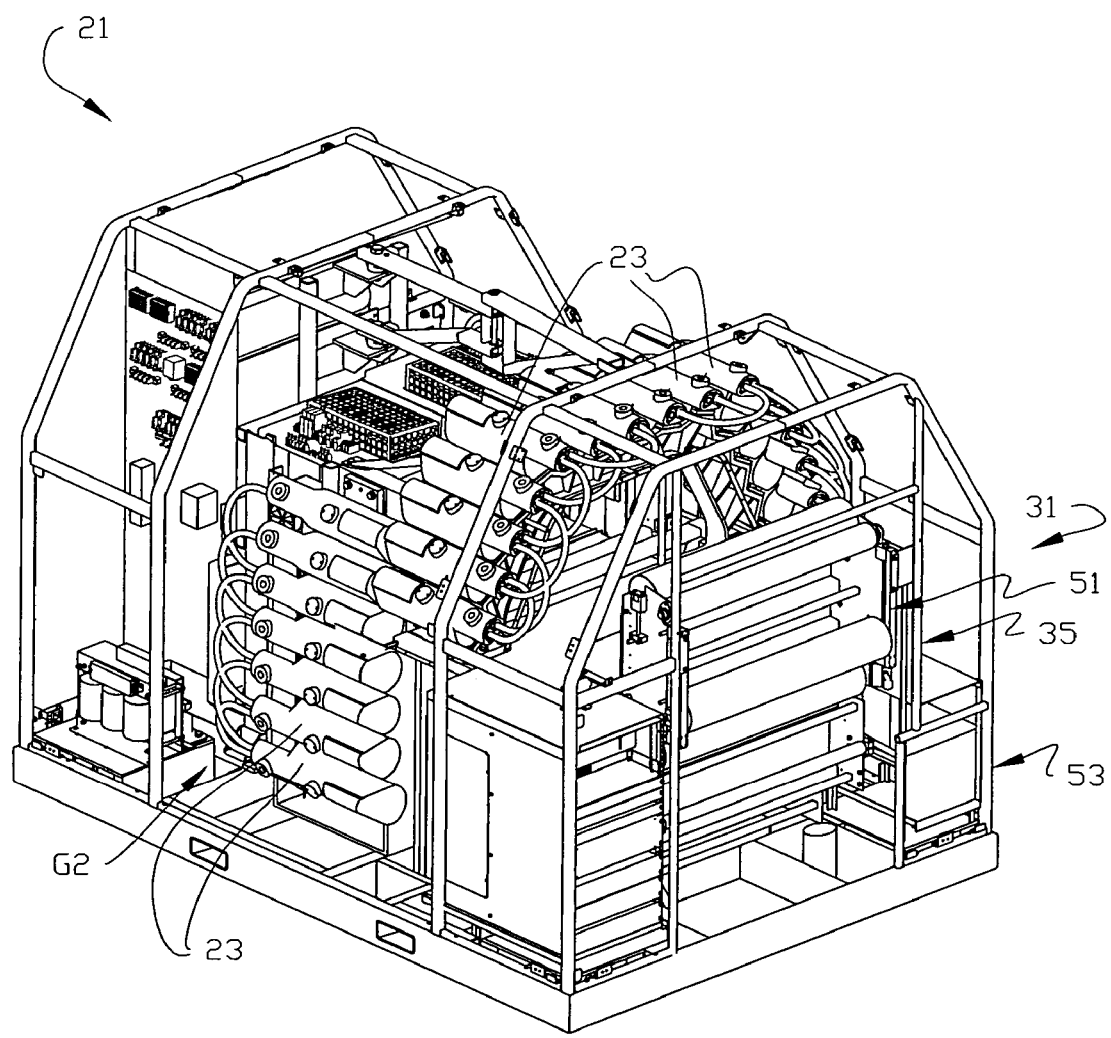
FIG. 2 is a rear perspective view of the imaging inspection apparatus for inspecting objects located within moving articles as shown in FIG. 1.
Figure 5:
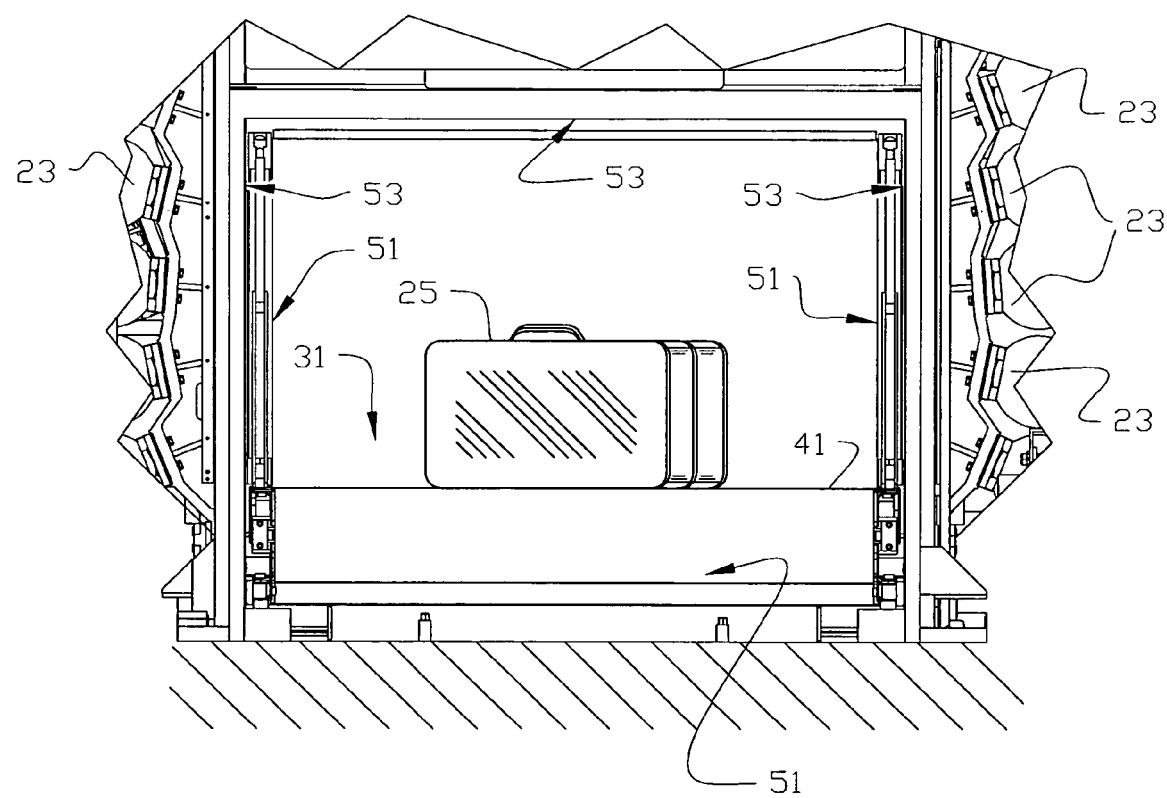
FIG. 5 is a partial end view of the apparatus of FIGS. 1 and 2, on an enlarged scale over the views of FIGS. 1–4, showing the spaced positioning relationship of the invention's conveyor relative to the remaining structure of the apparatus, according to one embodiment of the invention.

In FIGS. 1 and 2, there is illustrated an imaging inspection apparatus 21 according to one embodiment of the invention. As indicated, apparatus 21 is particularly designed for inspecting (and detecting) objects (not shown) which might be located within closed articles such as personal luggage of an airplane traveler. As such, the apparatus is ideally designed for placement and use within an airport or other transportation facility in which large numbers of such articles are received and transported. Apparatus 21 is adapted for inspecting and detecting concealed objects such as explosives, weapons, etc., including in solid and powder form. Further explanation of how apparatus operates is provided below. One example of such an article, this being a suitcase (luggage) 25, is shown in FIG. 5. Understandably, the apparatus inspects several such articles as these move therethrough.

Apparatus 21 includes a plurality of imaging inspection devices 23, which, in a preferred embodiment, are individual X-ray Computer Tomography (XRT) scanning devices. That is, each device is preferably an individual X-ray photon source, which are collimated to provide what may be referred to as a "fan beam." In one embodiment, these fan beams will each be collimated to a beam thickness of about 1 mm. over a distance of at least about 141 cm, with a divergence of about 0.7 milli-radians (or about 0.04. degree). Beams of such dimensions are preferred to substantially prevent background scatter and radiation leakage.

As seen in FIGS. 1 and 2, inspection devices 23 are arranged in three groupings G1, G2 and G3, with each grouping oriented in a particular orientation relative to the conveyor and thereby to the path of travel of the articles through the apparatus. Each grouping directs X-ray beams along a plane onto the articles, there thus being a total of three planes of beams (A, B and C, shown in FIGS. 3 and 4) each article passes through while being inspected. In one embodiment, groupings G1 and G2 each include seven devices 23, and direct beams from opposite sides of the apparatus in a substantially horizontal manner, such that each article passing through the apparatus will receive beams toward the sides thereof. Grouping G3 includes fourteen devices 23 and directs beams from the top of the apparatus downwardly onto the articles, so that said articles will receive beams on the tops thereof. Each article is thus subject to pluralities of beams on at least three sides thereof. As the articles move through the three scan planes A, B and C, a number of lines of projection image data are formed for the scanned article in each scan plane. These lines of projection image data show the attenuation of the X-rays by the article and the object(s) (if any) therein. The density of an object scanned within the package can be calculated from the attenuation of the X-rays caused by the object.

When multiple X-ray devices 23 such as shown are used and arranged in groupings each oriented in a substantially planar array, as also shown, devices located near the center of a side of the image area will provide a higher intensity beam on a detector array (located opposite the devices for each grouping, one grouping of such detectors being represented by the numeral 27 in FIG. 1) because intensity decreases with the square of d, the distance of the device (source) from the detector element. Since the output of the detector elements of the detector array for all source locations should be equal, in the absence of an article such as a suitcase 25, it is necessary to progressively reduce the current for source locations as these approach the center of a side of the image for straight line source arrays. The same effect of maximizing the dynamic range of the system by substantially equalizing the output of the detectors in the detector array can also be achieved by curving the source array to progressively increase the distance between the sources and the detector arrays as the sources approach the center of the image area. This configuration provides substantially better coverage of the image area. Detectors used in each grouping 27 (three total, to accommodate the three groups of devices 23) and capable of performing in the manner defined herein are preferably of conventional construction and thus known in the art. Further description of this operation is provided in the above-mentioned U.S. Pat. No. 6,236,709.

To adapt the system for multi-spectral XCT reconstruction, each detector array 27 outputs five energy levels for each scan to provide multiple energies for the same set of data points. As mentioned or understood from the foregoing patents, systems of this type which use multiple filters to obtain multi-energy outputs from a detector are known. Alternatively, the detector systems can be constructed so that each detector provides an output signal to five comparators, each of which receives a different threshold voltage from a threshold source. The output of each comparator is a different energy level signal which represents the intensity of the spectral range above the comparator threshold input. The proportional decrease in the number of photons is a function of material chemical composition (i.e. atomic number).

The processing and analysis assembly 28 (FIG. 1) for the imaging apparatus of the invention is preferably similar to that used in U.S. Pat. No. 6,236,709, mentioned above. This assembly receives inputs from a sensor unit which includes the detector arrays 27. A preprocessing unit interfaces directly with the sensor units to provide buffering of the output data received from the sensor units. Timing is controlled by an input from a shaft encoder. Once the five level input has been received and stored by the preprocessing unit from each of the detector arrays for a single scan, an address generator in the preprocessing unit which is connected to a plurality of reconstruction signal processing boards generates a board address to determine which of the reconstruction signal processing boards will receive a current frame of data. Each reconstruction board, as defined in U.S. Pat. No. 6,236,709, contains several (e.g., up to sixteen) computer chips. These systems cooperate to provide calibration and normalization of the raw input data, and then conventional multi-spectral XCT reconstruction which includes algebraic reconstruction. During this reconstruction, each slice through the article being inspected is reconstructed at five different energies which are required to obtain the atomic number of an inspected (sensed) object.

The algebraic reconstruction data is then sent to a detection and segmentation section of the apparatus which detects the atomic number and density of a scanned object located within one of the articles. For most materials, the linear X-ray attenuation coefficient mu is proportioned to the density. Thus the logarithm of the relative intensity of the X-ray beam is proportioned to the integral of the density of the material within the beam. The density and atomic number information is compared in a classification unit with information (criteria) within a reference table containing density and atomic number information for specific objects to be identified. This identification data and the reconstructed image data is then sent (preferably over a VME bus to a VME computer). The reconstructed XCT image data is displayed on the operator's console for review by the apparatus operator (and others, if desired). Processing of the data obtained from the scanning is preferably accomplished using the methodology (including the described ART algorithm, which employs a square grid of basis functions, centered at defined pixel locations all of the same form and diameter) described in U.S. Pat. No. 6,236,709, and further description is not believe necessary.

Figure 3:
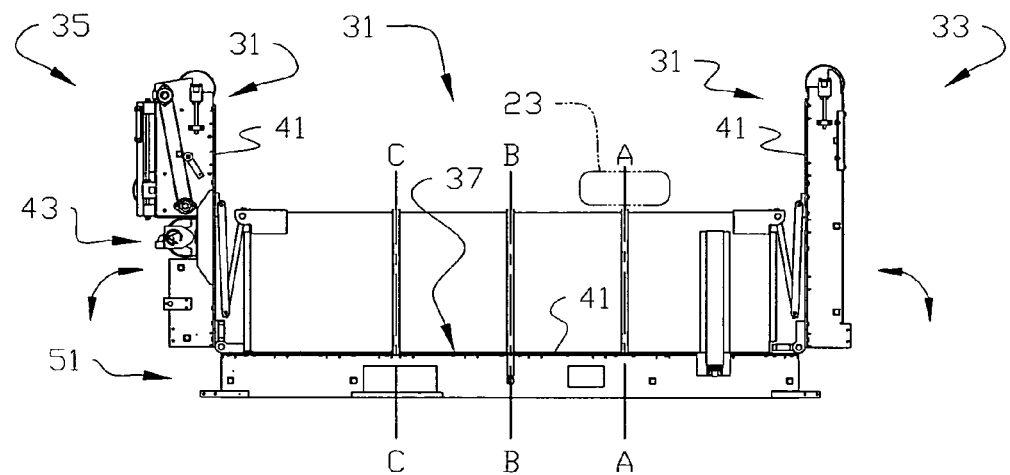
FIGS. 3 and 4 are side, elevational views, illustrating one embodiment of the conveyor of the invention in the raised (closed) and lowered (opened, operating) positions, respectively, FIG. 4 being smaller in scale.
Figure 4:
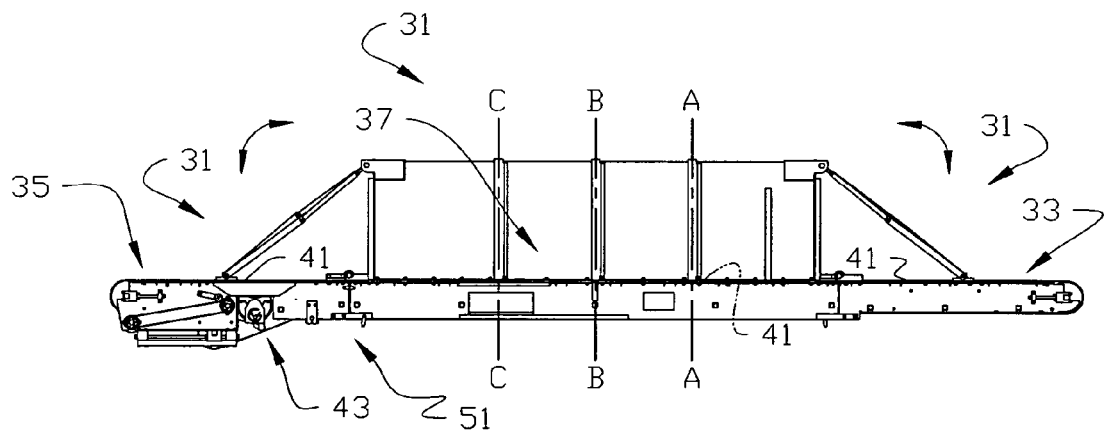

FIGS. 3–5 better illustrate the conveyor 31 of the invention. Conveyor 31 in accordance with a preferred embodiment of the invention, includes three portions, a main body portion 37, and two opposing end portions 33 and 35. End portion 33 is also seen in FIG. 1, while opposite end portion 35 is also seen in FIG. 2, both of these end portions 33 and 35 in FIGS. 1 and 2 being in the withdrawn, closed position. As such, these ends are substantially vertically oriented in an upward orientation relative to the substantially horizontal, main body portion 37 of conveyor 31. Also seen in FIGS. 3 and 4 are the three planes A, B and C, along which the groupings G1, G2 and G3 of devices 23 project their respective beams. Devices 23 are not shown in FIGS. 3 and 4 for ease of illustration, but it is understood from the above and FIGS. 1 and 2 that these devices would be positioned in a substantially planar grouping such that the planes A, B and C pass through substantially the center of a respective one of said groupings. One such device 23 is shown in phantom in FIG. 3 to illustrate this positioning orientation. Others are shown partly in FIG. 5, these forming part of groupings G1 and G2. The overhead devices of Grouping G3 are not shown in FIG. 5. As seen in FIGS. 3 and 4, each plane A, B and C passes through only main body portion 37 and not through either of the end portions 33 or 35. It is further seen in these FIGS. 3 and 4 that main body portion 37 does not include a gap therein; that is, the single belt 41 (see more below) used for the conveyor extends across the body portion 37 and does not include a gap or other form of opening therein.

Significantly, conveyor 31 is shown in FIG. 4 as being in its substantially flat (or planar) operating position to accept and pass (move) articles such as suitcase 25 there-along. In one embodiment, articles are placed on portion 33 and conveyed (moved) to the body portion 37 and finally to the remaining end portion 35, from which it is then removed (or drops off) the conveyor. During such movement, the article passes through planes A, B and C, where individual groupings of scans are taken. Very significantly, this movement occurs with substantially no adverse motion (e.g., excessive vibration) using the conveyor of this invention, such adverse motion, as explained above, possibly altering the readings of the scanned article. The invention accomplishes this unique motion using a single belt 41 and a single drive (motor) 43, while spacedly positioning the conveyor having these two components thereon upon a support deck structure 51 (see especially FIG. 5) separate from the frame structure 53 that holds the remainder of the apparatus, including particularly devices 23 and the detectors of each grouping 27. This spacing is best seen in FIG. 5. There is thus no need to synchronize multiple belts, thereby also reducing the complexity of the invention over many prior such apparatus. Of further notation, drive motor 43 is located on end portion 35, even further spacing it from the main support structure for the apparatus remainder. In this arrangement, articles are conveyed along at a constant speed, the belt sliding over the spacedly positioned and rigid (in a preferred embodiment, the support deck structure is made of steel) support deck structure 51 which assure accurate planarity of the belt during such movement. The above capability is made possible while also providing a conveyor structure which can be significantly reduced in length by folding of the two end portions to the closed, non-operating position, to facilitate shipping and other handling, as well as servicing and inspection, of apparatus 21. Understandably, these capabilities for the invention represent significantly advantageous features over complex apparatus such as described above.

In one embodiment of the invention as described above, drive motor 43 is a one horsepower, 480 VAC, three phase, reversible electric motor with rubber lagging for enhanced belt traction. The rollers used to carry the belt are each of about 6.5 inch diameter and crowned for belt tracking. The belt itself possesses a width of one meter (39.3 inches). The belt speed may vary from about 1.22 to about 36.6 meters per minute (or about four to 120 feet per minute). The motor speed is controlled using a variable frequency drive.

Thus there has been shown and described an imaging inspection apparatus which assures smooth movement of the articles being inspected such that effective scanning thereof will occur. The apparatus as defined herein is able to accomplish this while also allowing length reduction of the overall apparatus length by virtue of folding of the conveyor to a non-operating position. Although the example illustrated shows the conveyor in a substantially perpendicular orientation when in the "non-flat" orientation, this is not meant to limit the invention in that other angular orientations, both acute and obtuse, may be used. In a particular example, the conveyor's operational length while in the flat orientation was about 16.3 feet, and reduced to only about 10 feet when in the orientation shown. This represents a decrease in overall length of almost forty percent.

While there have been shown and described what are at present the preferred embodiments of the invention, it will be obvious to those skilled in the art that various changes and modifications may be made therein without departing from the scope of the invention as defined by the appended claims.

What is claimed is:

1. An imaging inspection apparatus for inspecting objects located within moving articles, said imaging inspection apparatus comprising:
    a single belt conveyor for conveying articles having objects located therein along a path of travel through an inspection location located substantially within said imaging inspection apparatus, said conveyor including a main portion and first and second end portions located on opposing ends of said main portion, said main portion and said first and second end portions adapted for being positioned in a substantially horizontal orientation during said conveying of said articles, said main portion of said conveyor not including a gap therein;
    a frame structure;
    a plurality of imaging inspection devices positioned on said frame and adapted for directing beams onto only said main portion of said conveyor and onto said articles as said articles move on said main portion of said conveyor and pass along said path of travel through said inspection location substantially within said imaging inspection apparatus to thereby inspect said articles, and for providing output signals as a result of said inspecting; and
    a processing and analysis assembly adapted for receiving said output signals from said plurality of imaging inspection devices and for analyzing said output signals to identify said objects within said moving articles, said conveyor not being physically coupled to said frame structure and also adapted for being folded such that said main portion is at said substantially horizontal orientation and said first and second end portions are each positioned in a substantially vertical, upward orientation when said conveyor is not conveying said articles along said path of travel during which said conveyor is of a lesser length in said horizontal orientation than when said main portion and said first and second end portions are in said substantially horizontal orientation.

2. The imaging inspection apparatus of claim 1 wherein said conveyor includes a support deck structure, said single belt conveyor moving over said support deck structure when said conveyor conveys said articles along said path of travel.

3. The imaging inspection apparatus of claim 2 wherein said conveyor further includes a single drive for driving said single belt.

4. The imaging inspection apparatus of claim 1 wherein said plurality of imaging inspection devices each comprise an X-ray computer tomography (XCT) scanning device and said beams are X-rays.

5. The imaging inspection apparatus of claim 4 wherein the number of said XCT scanning devices is within the range of from about twenty to about forty devices.

6. The imaging inspection apparatus of claim 4 wherein said XCT scanning devices are positioned on said frame in at least three groupings, each grouping of said XCT scanning devices adapted for directing said X-rays along a different plane onto said main portion of said conveyor within said inspection location located substantially within said imaging inspection apparatus.

7. The imaging inspection apparatus of claim 6 further including a plurality of X-ray detectors positioned on said frame and adapted for receiving said X-rays from selected ones of said XCT scanning devices as said X-rays pass through said articles on said conveyor as said articles move along said path of travel through said inspection location located substantially within said imaging inspection apparatus.

8. The imaging inspection apparatus of claim 6 wherein said XCT scanning devices of a first grouping of said three groupings are positioned substantially vertically above said inspection location located substantially within said imaging inspection apparatus, and said XCT scanning devices of second and third groupings of said three groupings are positioned along opposite sides of said inspection location located substantially within said imaging inspection apparatus.

9. The imaging inspection apparatus of claim 8 wherein the number of said XCT scanning devices in said first grouping is fourteen and the number of said XCT scanning devices in each of said second and third groupings is seven.

10. The imaging apparatus of claim 1 wherein said plurality of imaging inspection devices each comprise an X-ray computer tomography (XCT) scanning device and said beams are X-rays, said XCT scanning devices being positioned on said frame in at least three groupings, each grouping of said XCT scanning devices being positioned relative to said main portion of said conveyor and adapted for directing said X-rays along a different plane onto only said main portion within said inspection location located substantially within said imaging inspection apparatus, each of said planes being substantially perpendicular to said main portion.

11. The imaging inspection apparatus of claim 10 further including a plurality of X-ray detectors positioned on said frame relative to said main portion of said conveyor and adapted for receiving said X-rays from selected ones of said XCT scanning devices as said X-rays pass through said articles on said main portion of said conveyor as said articles move along said path of travel through said inspection location located substantially within said imaging inspection apparatus.

* * * * *